US012672970B2

(12) United States Patent
Folan et al.

(10) Patent No.: US 12,672,970 B2
(45) Date of Patent: Jul. 7, 2026

(54) STENT SYSTEM FOR MAINTAINING PATENCY OF A BODY LUMEN

(71) Applicant: BOSTON SCIENTIFIC SCIMED, INC., Maple Grove, MN (US)

(72) Inventors: Martyn G. Folan, Galway (IE); Jonathan Root, Townsend, MA (US); Louis McNern, Donegal (IE); Daniel Tuck, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 428 days.

(21) Appl. No.: 18/382,894

(22) Filed: Oct. 23, 2023

(65) Prior Publication Data

US 2024/0130872 A1    Apr. 25, 2024
US 2024/0225863 A9    Jul. 11, 2024

Related U.S. Application Data

(60) Provisional application No. 63/418,812, filed on Oct. 24, 2022.

(51) Int. Cl.
*A61F 2/852*    (2013.01)
*A61F 2/954*    (2013.01)
(Continued)

(52) U.S. Cl.
CPC .............. *A61F 2/852* (2013.01); *A61F 2/954* (2013.01); *A61F 2/962* (2013.01); *A61F 2002/826* (2013.01)

(58) Field of Classification Search
CPC .. A61F 2/954; A61F 2/88; A61F 2/962; A61F 2/852; A61M 27/002
See application file for complete search history.

(56) References Cited

U.S. PATENT DOCUMENTS 6,332,892 B1    12/2001    Desmond, III et al.
8,246,691 B2    8/2012    Mangiardi
(Continued)

FOREIGN PATENT DOCUMENTS

CN    114305791 A    4/2022
JP    2020526287 A    8/2020

OTHER PUBLICATIONS

International Search Report and Written Opinion for International Application No. PCT/US2023/035726, dated Feb. 6, 2024.

*Primary Examiner* — Christopher J Beccia
(74) *Attorney, Agent, or Firm* — Seager, Tufte & Wickhem, LLP

(57) ABSTRACT

A system for maintaining patency of a body lumen may include a first endoprosthesis configured to shift from a straightened configuration to a helical configuration defining a plurality of loops, and a second endoprosthesis configured to shift from a radially collapsed configuration toward a radially expanded configuration. The plurality of loops defines a passage having an inner diameter. At least a portion of the second endoprosthesis is disposed within the passage in the radially expanded configuration. A method of maintaining patency of a body lumen may include advancing a first endoprosthesis into a first body lumen in a straightened configuration, deploying the first endoprosthesis within the first body lumen in a helical configuration defining a plurality of loops, advancing a second endoprosthesis into the first body lumen in a radially collapsed configuration, and shifting the second endoprosthesis to a radially expanded configuration within the plurality of loops.

20 Claims, 7 Drawing Sheets

(51) Int. Cl.
    *A61F 2/962*        (2013.01)
    *A61F 2/82*         (2013.01)

(56)           References Cited

U.S. PATENT DOCUMENTS

| | | | |
|---|---|---|---|
| 8,603,185 B2 * | 12/2013 | Shah | A61M 27/008 |
| | | | 623/23.64 |
| 9,415,196 B2 | 8/2016 | Jordan | |
| 9,539,126 B2 | 1/2017 | Walsh et al. | |
| 9,675,475 B2 | 6/2017 | Walsh et al. | |
| 9,839,508 B2 | 12/2017 | Walsh et al. | |
| 10,117,760 B2 | 11/2018 | Mangiardi | |
| 10,130,460 B2 | 11/2018 | Kang et al. | |
| 10,245,165 B2 | 4/2019 | Mangiardi | |
| 10,357,387 B2 | 7/2019 | Walsh et al. | |
| 10,406,007 B2 | 9/2019 | Walsh et al. | |
| 10,500,035 B2 * | 12/2019 | Walsh | A61M 27/002 |
| 10,888,410 B2 | 1/2021 | Nolan et al. | |
| 11,229,536 B2 | 1/2022 | Walsh et al. | |
| 11,246,699 B2 | 2/2022 | Spindler et al. | |
| 2001/0027341 A1 | 10/2001 | Gianotti | |
| 2002/0091440 A1 | 7/2002 | Calcote | |
| 2002/0179166 A1 | 12/2002 | Houston et al. | |
| 2005/0154448 A1 | 7/2005 | Cully et al. | |
| 2007/0123969 A1 | 5/2007 | Gianotti | |
| 2007/0282453 A1 | 12/2007 | Weitzner et al. | |
| 2009/0093889 A1 | 4/2009 | Ducharme | |
| 2009/0276029 A1 | 11/2009 | Caro et al. | |
| 2010/0030321 A1 | 2/2010 | Mach | |
| 2010/0100170 A1 | 4/2010 | Tan et al. | |
| 2010/0256731 A1 | 10/2010 | Mangiardi | |
| 2011/0213453 A1 | 9/2011 | Mangiardi | |
| 2014/0277561 A1 * | 9/2014 | Jordan | A61F 2/04 |
| | | | 623/23.7 |
| 2015/0223953 A1 | 8/2015 | Pendleton et al. | |
| 2015/0250579 A1 * | 9/2015 | Howard | A61F 2/04 |
| | | | 623/23.7 |
| 2016/0302910 A1 | 10/2016 | Jordan | |
| 2019/0053921 A1 | 2/2019 | Mangiardi | |

* cited by examiner

STENT SYSTEM FOR MAINTAINING PATENCY OF A BODY LUMEN

CROSS REFERENCE TO RELATED APPLICATIONS

This application claims the benefit of and priority to U.S. Provisional Patent Application Ser. No. 63/418,812, filed on Oct. 24, 2022, the disclosure of which is incorporated herein by reference.

TECHNICAL FIELD

The present disclosure pertains to medical devices, and methods for manufacturing and/or using medical devices. More particularly, the present disclosure pertains to an improved design for a stent system for maintaining patency of a body lumen at a bifurcation.

BACKGROUND

One currently known treatment for relief of biliary blockage in the biliary tree is the placement of a covered endoprosthesis or stent within the restricted body lumen (e.g., the bile duct, the pancreatic duct, etc.), such as that caused by a stricture formation. For example, it may be necessary to open the body lumen (e.g., the bile duct, the pancreatic duct, etc.) to permit passing of bile and stone-related debris to relieve acute painful symptoms. Additionally, the biliary tree has several branches, bifurcations, and/or adjoining lumens. Placement of a covered endoprosthesis or stent across a bifurcation and/or an opening of an adjacent branch or lumen to treat a stricture or blocked body lumen may result in additional blockage of a currently open or unrestricted lumen, which may be undesirable. There is an ongoing need to provide alternative endoprostheses or stents as well as alternative methods for manufacturing and using endoprostheses or stents.

SUMMARY

In one example, a system for maintaining patency of a body lumen may comprise a first endoprosthesis having a lumen extending from a first end to a second end, wherein the first endoprosthesis is configured to shift from a straightened configuration to a helical configuration defining a plurality of loops; and a second endoprosthesis configured to shift from a radially collapsed configuration toward a radially expanded configuration. The plurality of loops may define a passage having an inner diameter. At least a portion of the second endoprosthesis may be disposed within the passage in the radially expanded configuration.

In addition or alternatively to any example described herein, at least a portion of the second endoprosthesis extends away from the passage when the second endoprosthesis is disposed within the passage in the radially expanded configuration.

In addition or alternatively to any example described herein, at least a portion of the first endoprosthesis extends away from the plurality of loops.

In addition or alternatively to any example described herein, a first end portion of the first endoprosthesis extends away from the second endoprosthesis transversely relative to a central longitudinal axis of the second endoprosthesis when the second endoprosthesis is disposed within the passage in the radially expanded configuration.

In addition or alternatively to any example described herein, a second end portion of the first endoprosthesis extends away from the second endoprosthesis generally parallel to a central longitudinal axis of the second endoprosthesis when the second endoprosthesis is disposed within the passage in the radially expanded configuration.

In addition or alternatively to any example described herein, the first endoprosthesis is formed from a polymeric material.

In addition or alternatively to any example described herein, a system for maintaining patency of a body lumen may comprise a first endoprosthesis having a lumen extending from a first end to a second end, wherein the first endoprosthesis is configured to shift from a straightened configuration to a helical configuration defining a plurality of loops; and a second endoprosthesis configured to shift from a radially collapsed configuration toward a radially expanded configuration. The plurality of loops may define a passage having an inner diameter. The second endoprosthesis may be configured to be disposed within the passage. The second endoprosthesis may have an outer diameter in the radially expanded configuration. The outer diameter of the second endoprosthesis may be within 20% of the inner diameter of the passage.

In addition or alternatively to any example described herein, the plurality of loops defines an outer diameter between about 6 French and about 12 French.

In addition or alternatively to any example described herein, the first endoprosthesis is self-biased toward the helical configuration.

In addition or alternatively to any example described herein, the second endoprosthesis is self-biased toward the radially expanded configuration.

In addition or alternatively to any example described herein, the second endoprosthesis includes a polymeric covering extending along at least a portion of its length.

In addition or alternatively to any example described herein, the first endoprosthesis includes a corrugated section disposed between the first end and the plurality of loops.

In addition or alternatively to any example described herein, the first endoprosthesis includes one or more drainage holes extending through a side wall of the first endoprosthesis.

In addition or alternatively to any example described herein, the first endoprosthesis includes one or more anti-migration elements extending radially outward therefrom.

In addition or alternatively to any example described herein, a method of maintaining patency of a body lumen may comprise advancing a first endoprosthesis into a first body lumen in a straightened configuration; deploying the first endoprosthesis within the first body lumen in a helical configuration defining a plurality of loops; advancing a second endoprosthesis into the first body lumen in a radially collapsed configuration; and shifting the second endoprosthesis to a radially expanded configuration within the plurality of loops.

In addition or alternatively to any example described herein, advancing the first endoprosthesis into the first body lumen in the straightened configuration includes positioning a first end portion of the first endoprosthesis in a second body lumen adjacent the first body lumen.

In addition or alternatively to any example described herein, the first end portion of the first endoprosthesis extends away from the second endoprosthesis transversely relative to a central longitudinal axis of the second endoprosthesis when the second endoprosthesis is disposed within the plurality of loops in the radially expanded configuration In addition or alternatively to any example described herein, the first endoprosthesis is self-biased toward the helical configuration when unconstrained.

In addition or alternatively to any example described herein, the first endoprosthesis is constrained in the straightened configuration by a guidewire when advancing the first endoprosthesis into the first body lumen.

In addition or alternatively to any example described herein, the first endoprosthesis is constrained in the straightened configuration by a delivery sheath when advancing the first endoprosthesis into the first body lumen.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
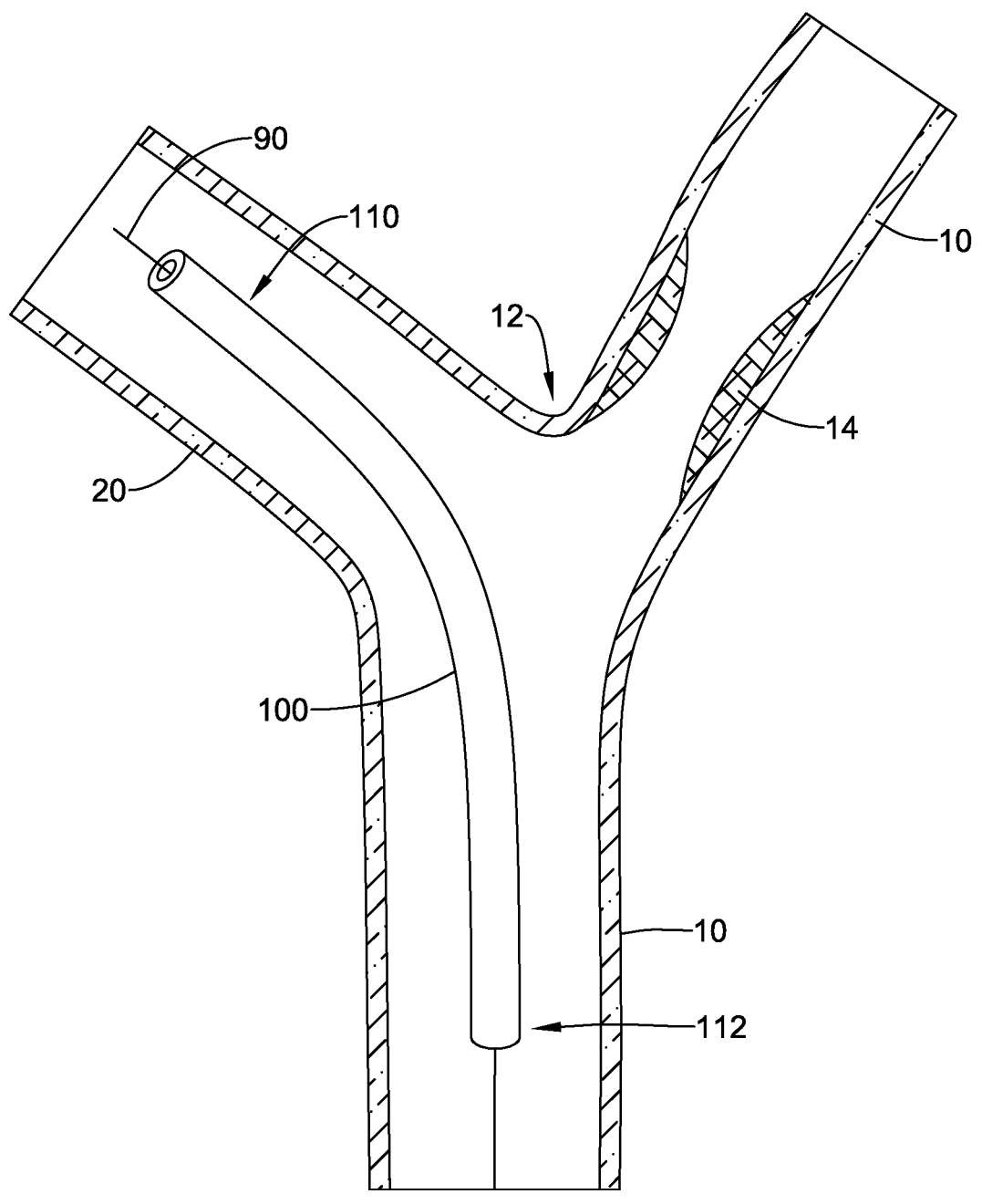
FIGS. 1-4 illustrate selected aspects of a stent system for maintaining patency of a body lumen and a method of using the stent system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension according to the intended usage, unless the extent or dimension in question is preceded by or identified as a "minimum", which may be understood to mean the smallest measurement of the stated or identified dimension according to the intended usage. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of a system. It should be noted that in any given figure, some features of the system may not be shown, or may be shown schematically, for simplicity. Additional details regarding some of the components of the system may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. As such, it will be understood that the following discussion may apply equally to any and/or all of the components for which there are more than one within the system, unless explicitly stated to the contrary. Additionally, not all instances of some elements or features may be shown in each figure for clarity.

FIG. 1 illustrates selected features of a first body lumen 10 and a second body lumen (e.g., a branch lumen) adjacent the first body lumen 10. In some examples, the first body lumen 10 and the second body lumen 20 may converge at a bifurcation 12. Said differently, the second body lumen 20 may branch off of or diverge from the first body lumen 10 at the bifurcation 12, or the first body lumen 10 may branch off of or diverge from the second body lumen 20 at the bifurcation 12. Thus, the first body lumen 10 and the second body lumen 20 may meet or be joined at the bifurcation 12. As shown in FIG. 1, the first body lumen 10 may include a stricture 14 (e.g., a blockage) disposed along an inner surface of the wall of the first body lumen 10. As shown in FIG. 1, the stricture 14 may be located upstream of the bifurcation 12 for example. However, in other instances, the stricture 14 may be located downstream of the bifurcation 12. Placement of a covered endoprosthesis or stent within stricture 14 formed in the first body lumen 10 may result in a partial or complete blockage of the second body lumen 20 because of the covered endoprosthesis or stent spanning the bifurcation 12. Thus, fluid flowing from the second body lumen 20 may be prevented from flowing downstream into the first body lumen 10. It may be desirable to maintain patency of the second body lumen 20 when treating the first body lumen 10 to permit fluid to flow from the second body lumen 20 into the first body lumen 10.

A method of maintaining patency of a body lumen using a system disclosed herein may include advancing a guidewire 90 into the first body lumen 10. In some embodiments, the method may further include advancing the guidewire 90 into the second body lumen 20 from the first body lumen 10, upstream of the bifurcation 12. The method may include advancing a first endoprosthesis 100 into the first body lumen 10 in a straightened configuration over the guidewire 90, as seen in FIG. 1. It shall be understood that the term "endoprosthesis" as used herein may be used interchangeably with the term "stent". In some embodiments, the first endoprosthesis 100 may be constrained in a straightened configuration by the guidewire 90 when advancing the first endoprosthesis 100 through the first body lumen 10 and into the second body lumen 20. In some alternative embodiments, the first endoprosthesis 100 may be constrained in the straightened configuration by a delivery sheath (not shown) surrounding the first endoprosthesis 100 when advancing the first endoprosthesis 100 through the first body lumen 10 and into the second body lumen 20. Other configurations, including combinations thereof, are also contemplated.

In some embodiments, advancing the first endoprosthesis 100 through the first body lumen 10, downstream of the bifurcation 14, and into the second body lumen 20 in the straightened configuration may include positioning a first end portion 110 of the first endoprosthesis 100 in the second body lumen 20, such as upstream of the bifurcation 12, with a second end portion 112 of the first endoprosthesis 100 remaining in the first body lumen 10, such as downstream of the bifurcation 12, as seen in FIG. 1.

Figure 2:
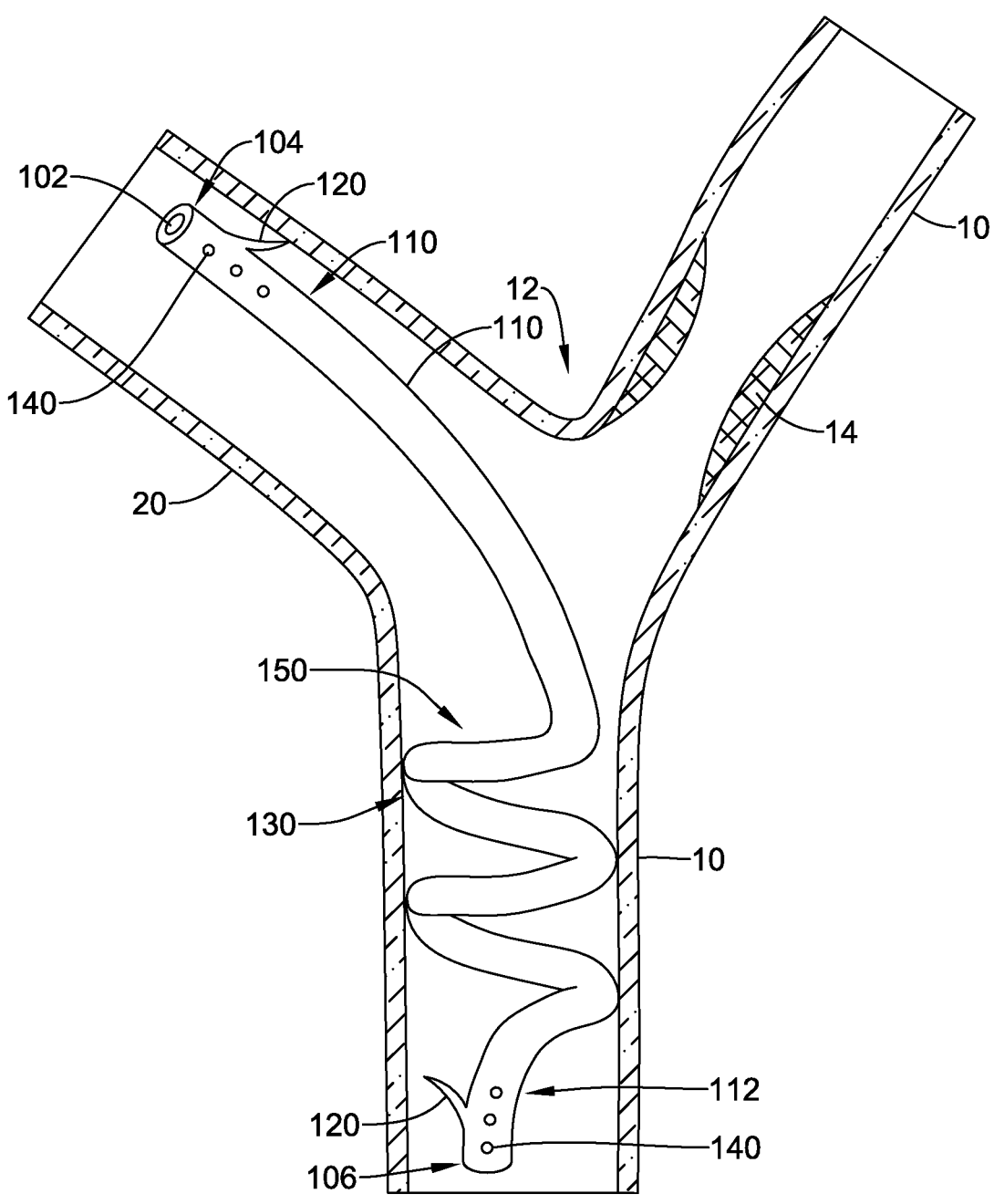

The method may include deploying the first endoprosthesis 100 into a helical configuration with the first end portion 110 of the first endoprosthesis 100 in the second body lumen 20, such as upstream of the bifurcation 12, and the second end portion 112 of the first endoprosthesis 100 in the first body lumen 10, such as downstream of the bifurcation 12. Accordingly, a medial portion of the first endoprosthesis 100 may be located at the bifurcation 12 when deployed into the helical configuration. When deployed into the helical configuration, the medial portion of the first endoprosthesis 100 may define a plurality of helical loops 130, as seen in FIG. 2. As shown in FIG. 2, the first endoprosthesis 100 may be deployed at the bifurcation with the plurality of helical loops 130 positioned in the first body lumen 10 proximal (e.g., downstream) of the bifurcation 12 and the first end region 110 of the endoprosthesis 100 in the second body lumen 10 distal (e.g., upstream) of the bifurcation 12. In the deployed, helical configuration, the radially outer extent of the helical loops 130 may contact and/or press radially outward against the inner surface of the first body lumen 10. The first endoprosthesis 100 may be configured to automatically shift from the straightened configuration (in which the helical loops 130 are straightened or elongated) when constrained by the guidewire 90 (or an outer sheath, if present) to the helical configuration (e.g., FIGS. 2, 5) when unconstrained. In at least some embodiments, the first endoprosthesis 100 may be self-biased toward the helical configuration when unconstrained.

Figure 5:
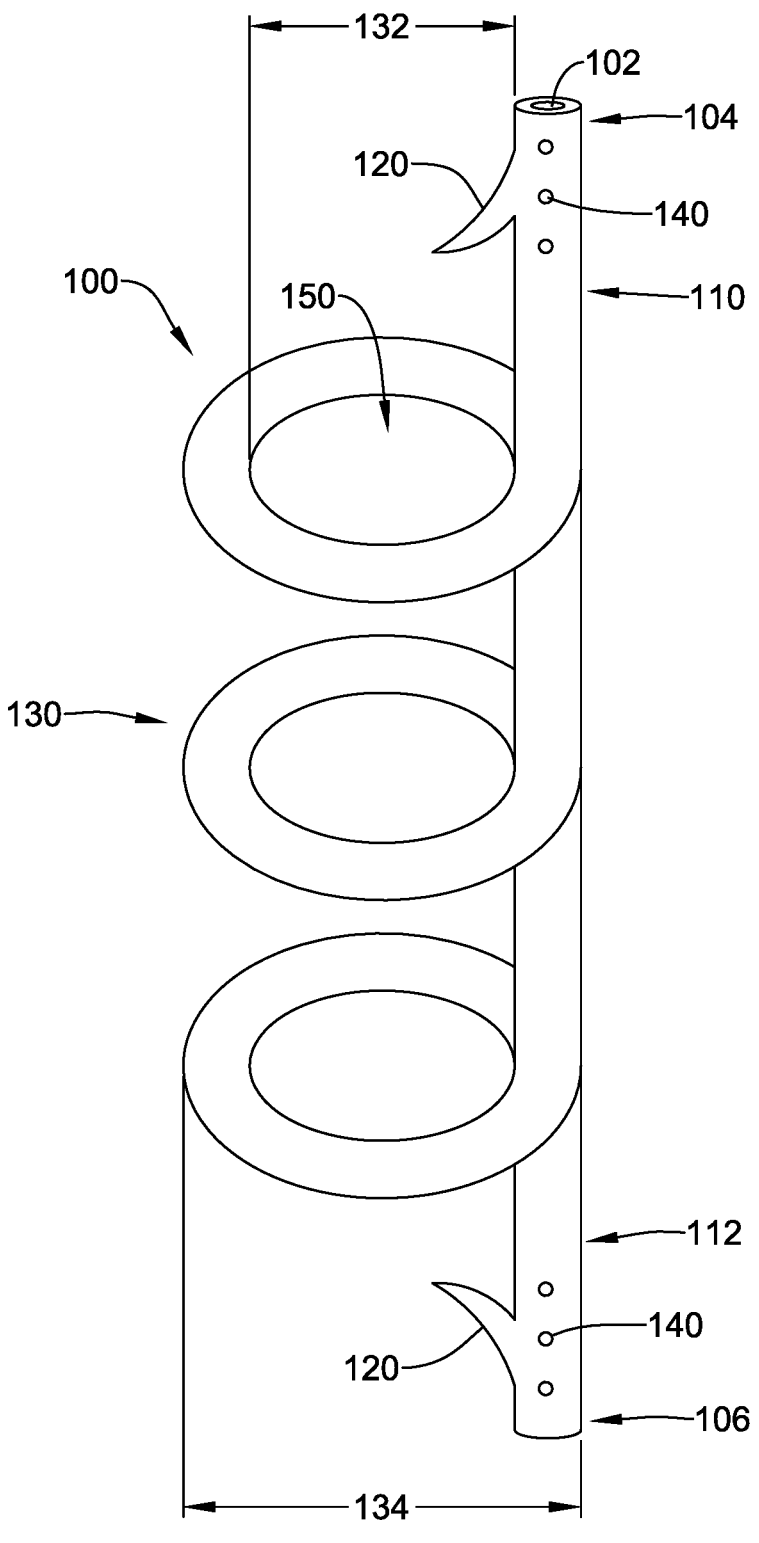
FIG. 5 illustrates selected aspects of a stent of the stent system of FIGS. 1-4.

Turning briefly to FIG. 5, which illustrates selected aspects of the first endoprosthesis 100 in more detail, the first endoprosthesis 100 may have a lumen 102 extending from a first end 104 to a second end 106. In some embodiments, during use, the first end 104 may be a distal end of the first endoprosthesis 100 and the second end 106 may be a proximal end of the first endoprosthesis 100, although this is not required.

In some embodiments, at least a portion of the first endoprosthesis 100 may extend away from the plurality of helical loops 130 in the helical configuration. In some embodiments, the first end portion 110 may extend away from the plurality of helical loops 130 in the helical configuration. In some embodiments, the first end portion 110 may extend from the plurality of helical loops 130 to the first end 104 of the first endoprosthesis 100. In some embodiments, a second end portion 112 may extend away from the plurality of helical loops 130 in the helical configuration. In some embodiments, the second end portion 112 may extend from the plurality of helical loops 130 to the second end 106 of the first endoprosthesis 100.

In some embodiments, the first endoprosthesis 100 may include one or more anti-migration elements 120. In some embodiments, the one or more anti-migration elements 120 may be integrally and/or monolithically formed with the first endoprosthesis 100. In some embodiments, the one or more anti-migration elements 120 may be configured to be positioned substantially flush with an outer surface of the first endoprosthesis 100 in the straightened configuration (e.g., when the first endoprosthesis 100 is constrained in the straightened configuration) and/or during advancement and/or delivery into the first body lumen 10, as seen in FIG. 1.

In some embodiments, the one or more anti-migration elements 120 may be configured to extend radially outward from the first endoprosthesis 100 in the helical configuration and/or when unconstrained, as seen in FIGS. 2 and 5. In some embodiments, the one or more anti-migration elements 120 may be disposed within the first end portion 110 and/or the second end portion 112. In some embodiments, one (or more) of the one or more anti-migration elements 120 may be disposed within the first end portion 110 and one (or more) of the one or more anti-migration elements 120 may be disposed within the second end portion 112. In some embodiments, the one or more anti-migration elements 120 may be disposed only within the first end portion 110. In some embodiments, the one or more anti-migration elements 120 may be disposed only within the second end portion 112. In some embodiments, the one or more anti-migration elements 120 may be self-biased to extend radially outward from the first endoprosthesis 100 in the helical configuration. In some embodiments, the first endoprosthesis 100 may include a mechanism configured to bias the one or more anti-migration elements 120 to extend radially outward from the first endoprosthesis 100 in the helical configuration. Other configurations are also contemplated. The one or more anti-migration elements 120 may be configured to engage an inner surface of a body lumen that the first endoprosthesis

100 is disposed in (e.g., the one or more anti-migration elements 120 may be configured to engage an inner surface of the first body lumen 10 and/or the second body lumen 20). In some instances, the anti-migration elements 120 may be barbs extending from the tubular wall of the first endoprosthesis. In other embodiments, the anti-migration elements 120 may be a pigtail or helical anchor located at the first end portion 110 and/or the second end portion 112.

Again referring to FIG. 5, in some embodiments, the first endoprosthesis 100 may include one or more drainage ports 140 extending through a side wall of the first endoprosthesis 100. The one or more drainage ports 140 may be in fluid communication with the lumen 102. The one or more drainage ports 140 may be disposed along the first end portion 110, the second end portion 112, and/or the plurality of helical loops 130. While illustrated in FIG. 5 as being disposed along the first end portion 110 and the second end portion 112, in some embodiments, the one or more drainage ports 140 may be disposed only along the first end portion 110, only along the second end portion 112, and/or only along the plurality of helical loops 130. In some embodiments, the one or more drainage ports 140 may be disposed along substantially an entire length of the first endoprosthesis 100, or along any portion thereof.

In some embodiments, the plurality of helical loops 130 defines a passage 150 having an inner diameter 132. In some embodiments, the plurality of helical loops 130 may extend circumferentially around the passage 150 and/or a longitudinal axis of the passage 150. In at least some embodiments, the plurality of helical loops 130 may extend helically around the passage 150 and/or the longitudinal axis of the passage 150 in the helical configuration.

The passage 150 may be outlined by an inner extent of the plurality of helical loops 130 as defined by the outer surface of the tubular wall of the first endoprosthesis 100. The plurality of helical loops 130 may define an outer diameter 134 and/or an outermost extent defined by the outer surface of the tubular wall of the first endoprosthesis 100. In some embodiments, the outer diameter 134 and/or the outermost extent of the plurality of helical loops 130 may be between about 6 French (Fr) to about 15 Fr (e.g., about 2 millimeters to about 5 millimeters). In some embodiments, the outer diameter 134 and/or the outermost extent of the plurality of helical loops 130 may be between about 6 Fr to about 12 Fr (e.g., about 2 millimeters to about 4 millimeters). In some embodiments, the outer diameter 134 and/or the outermost extent of the plurality of helical loops 130 may be about 6 Fr (e.g., about 2 millimeters), about 7 Fr (e.g., about 2.33 millimeters), about 8 Fr (e.g., about 2.67 millimeters), about 9 Fr (e.g., about 3 millimeters), about 10 Fr (e.g., about 3.33 millimeters), about 11 Fr (e.g., about 3.67 millimeters), about 12 Fr (e.g., about 4 millimeters), about 13 Fr (e.g., about 4.33 millimeters), about 14 Fr (e.g., about 4.67 millimeters), about 15 Fr (e.g., about 5 millimeters), etc.

In some embodiments, the elongate tube of the first endoprosthesis 100 may have a first overall length in the straightened configuration of about 40 millimeters to about 300 millimeters, about 50 millimeters to about 275 millimeters, about 60 millimeters to about 250 millimeters, about 80 millimeters to about 225 millimeters, about 100 millimeters to about 200 millimeters, about 110 millimeters to about 175 millimeters, or another suitable range.

In at least some embodiments, the first endoprosthesis 100 may be formed from a polymeric material. For example, the first endoprosthesis 100 may be formed of a polymeric tubular member extending from the first end 104 to the second end 106 of the first endoprosthesis 100. The polymeric tubular member may maintain a constant diameter as the first endoprosthesis 100 transitions between the straightened configuration to the helical configuration. In other words, the polymeric tubular member may be a polymer tube that does not appreciably radially expand as the first endoprosthesis 100 transitions between the straightened configuration to the helical configuration, thus retaining a constant diameter of the polymeric tubular member. The polymeric tubular member may be formed (e.g., heat set) to include the helical loops 130 along a medial region of the polymeric tubular member when unconstrained. When the polymeric tubular member is elongated, and thus straightened, the helical loops 130 may disappear to provide the straightened configuration when constrained for delivery to the bifurcation 12. Some suitable but nonlimiting examples of materials for the first endoprosthesis 100 are described herein.

Figure 3:
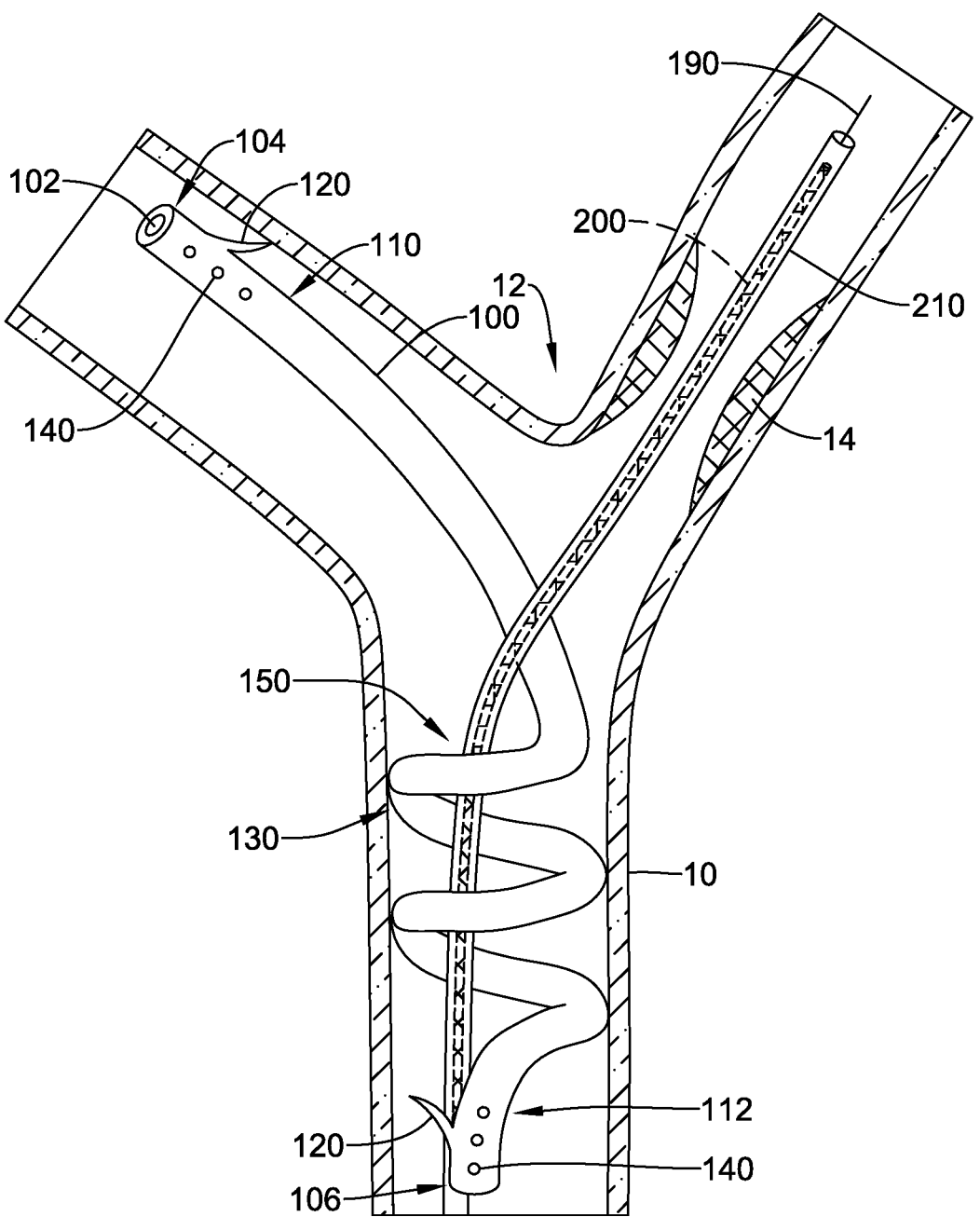

Turning now to FIG. 3, once the first endoprosthesis 100 has been delivered and expanded into the helical configuration across the bifurcation 12, the method may then include advancing a guidewire 190 into the first body lumen 10. The method may further include advancing the guidewire 190 into and/or through the plurality of helical loops 130 and/or through the passage 150 of the first endoprosthesis 100 subsequent to deploying the first endoprosthesis into the helical configuration. The method may further include advancing a second endoprosthesis 200 into the first body lumen 10 over the guidewire 190 in a radially collapsed configuration. Thus, the second endoprosthesis 200 may be placed within the helical loops 130 in a radially constrained or collapsed configuration such that the helical loops 130 surround the radially constrained or collapsed second endoprosthesis 200 with the second endoprosthesis 200 extending from a portion of the first body lumen 10 proximal (e.g., downstream) of the bifurcation 12 to a portion of the first body lumen 10 distal (e.g., upstream) of the bifurcation 12. The second endoprosthesis 200 may be positioned such that a distal end region of the second endoprosthesis 200 may extend across the stricture 14 (in the first body lumen 10 upstream of the bifurcation 12) in the radially constrained or collapsed configuration while a proximal end region of the second endoprosthesis 200 passes through the helical loops 130 of the first endoprosthesis 100 in the first body lumen 10 downstream of the bifurcation 12.

Figure 4:
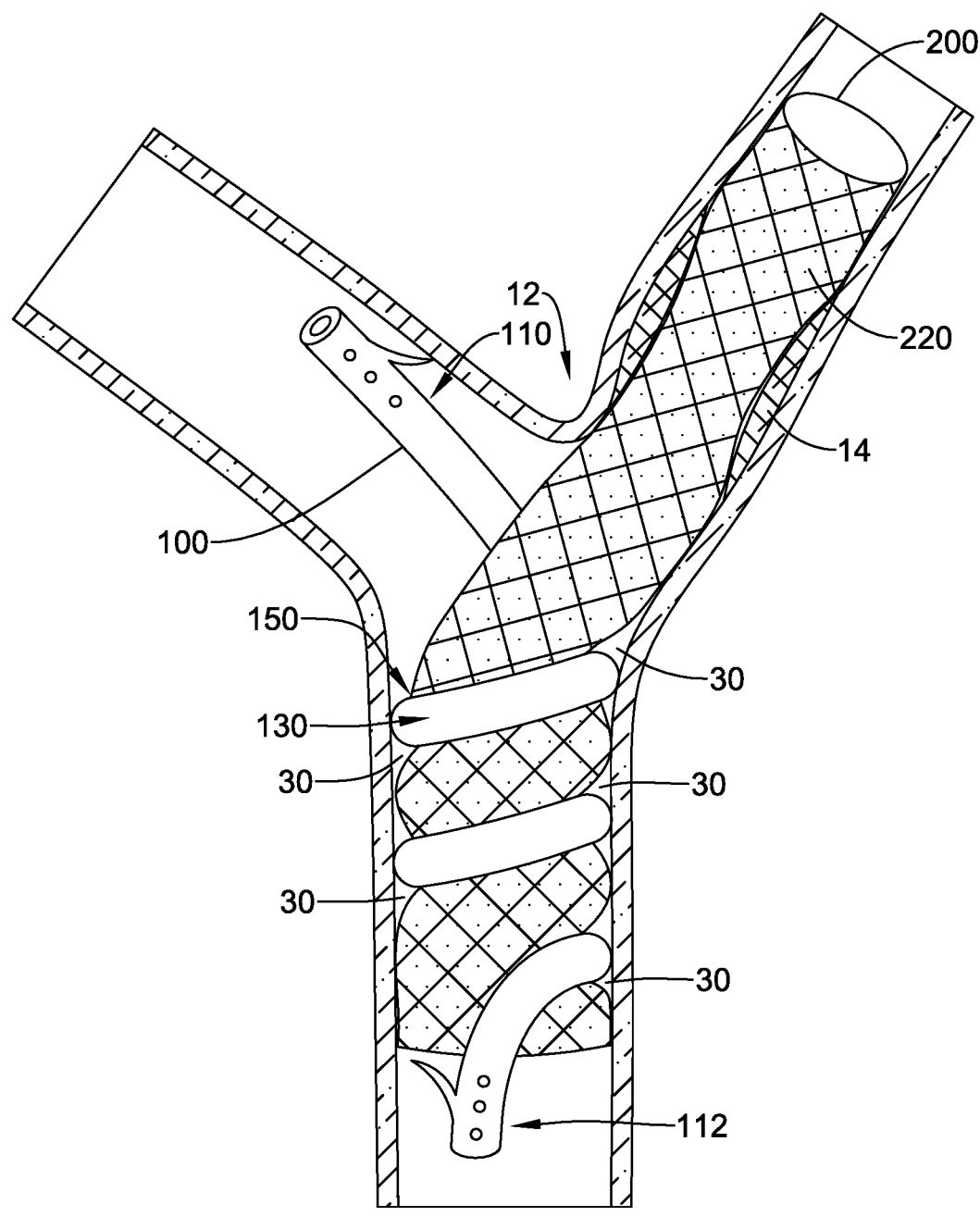

The second endoprosthesis 200 may be configured to shift from the radially collapsed configuration toward a radially expanded configuration (e.g., FIG. 4). In at least some embodiments, the second endoprosthesis 200 may be self-biased toward the radially expanded configuration. In some embodiments, the second endoprosthesis 200 may be formed from a superelastic and/or shape memory material, such as nitinol. In some embodiments, the second endoprosthesis 200 may be constrained in the radially collapsed configuration by the properties of the shape memory material when advancing the second endoprosthesis 200 into the first body lumen 10. In some embodiments, the second endoprosthesis 200 may be constrained in the radially collapsed configuration by a delivery sheath 210 surrounding the second endoprosthesis 200 when advancing the second endoprosthesis 200 into the first body lumen 10, as seen in FIG. 3. Other configurations, including combinations thereof, are also contemplated.

The second endoprosthesis 200 may include an expandable framework extending axially from a first end, which may be considered a proximal end in some instances, to a second end, which may be considered a distal end in some instances, along a central longitudinal axis of the second endoprosthesis 200 and/or the expandable framework. In at least some embodiments, the second endoprosthesis 200 and/or the expandable framework may be self-expandable when unconstrained. In some embodiments, the second endoprosthesis 200 and/or the expandable framework may be mechanically expandable. For example, the second endoprosthesis 200 and/or the expandable framework may be expandable using an inflatable balloon, using an actuation member, or other suitable means.

The expandable framework may include and/or be formed with a plurality of cells. In some embodiments, the expandable framework may include and/or be formed from one or more filaments interwoven around the central longitudinal axis of the second endoprosthesis 200 and/or the expandable framework. In at least some embodiments, the one or more filaments may form and/or define the plurality of cells. In some embodiments, the expandable framework may be braided, knitted, or woven from the one or more filaments. In some embodiments, the one or more filaments may be wires, threads, strands, etc. In some embodiments, adjacent filaments of the one or more filaments may define the cells (i.e., openings or interstices) through a wall of the expandable framework. Alternatively, in some embodiments, the expandable framework may be a monolithic structure formed from a cylindrical tubular member, such as a single, cylindrical laser-cut nickel-titanium (e.g., nitinol) tubular member, in which the remaining (e.g., unremoved) portions of the tubular member form the stent struts and/or framework with cells (i.e., openings or interstices) defined therebetween.

The second endoprosthesis 200 and/or the expandable framework may be substantially tubular and/or may include and/or define a lumen extending axially therethrough along the central longitudinal axis of the second endoprosthesis 200 and/or the expandable framework from the first end to the second end. In some embodiments, the second endoprosthesis 200 and/or the expandable framework may have an axial length of about 20 millimeters to about 200 millimeters, about 30 millimeters to about 175 millimeters, about 40 millimeters to about 150 millimeters, about 50 millimeters to about 125 millimeters, about 75 millimeters to about 100 millimeters, or another suitable range. In some embodiments, the second endoprosthesis 200 and/or the expandable framework may have an outer diameter of about 0.5 millimeters to about 5 millimeters, about 0.75 millimeters to about 4.5 millimeters, about 1 millimeters to about 4 millimeters, about 1.5 millimeters to about 3.5 millimeters, or another suitable range. In some embodiments, the second endoprosthesis 200 and/or the expandable framework may have an outer diameter of about 4 millimeters to about 28 millimeters, about 4 millimeters to about 14 millimeters, about 14 millimeters to about 28 millimeters, and/or other subsets thereof. Other configurations are also contemplated. Some suitable but non-limiting materials for the second endoprosthesis 200, the expandable framework, and/or components or elements thereof, for example metallic materials and/or polymeric materials, are described below.

In some embodiments, the first overall length of the elongate tube of the first endoprosthesis 100 in the straightened configuration may be related to the axial length of the second endoprosthesis 200. As shown and/or discussed herein, at least part of the first end portion 110 and the second end portion 112 of the first endoprosthesis 100 may extend proximal and distal of the second endoprosthesis 200, respectively. In some embodiments, the first overall length of the first endoprosthesis 100 in the straightened configuration may be approximated as the axial length of the second endoprosthesis 200 plus (a circumference of the second endoprosthesis 200 times the number of helical loops in the plurality of helical loops 130) plus the lengths of the first end portion 110 and the second end portion 112 of the first endoprosthesis 100 extending away from their respective ends of the second endoprosthesis 200.

The approximate overall length of the elongate tube of the first endoprosthesis 100 in the helical configuration will be less than the first overall length. In one nonlimiting example, the axial length of the second endoprosthesis 200 may be about 100 millimeters and the outer diameter of the second endoprosthesis 200 may be about 10 millimeters. One example for the first endoprosthesis 100 that may be associated and/or used with the example of the second endoprosthesis 200 described above may have a first overall length in the straightened configuration of about 300 millimeters and an approximate overall length in the helical configuration of about 120 millimeters. Other configurations and/or examples are also contemplated.

In some embodiments, the expandable framework may include a first flared portion proximate the first end of the expandable framework. The first flared portion may extend from the first end toward the second end. In some embodiments, the expandable framework may include a second flared portion proximate the second end of the expandable framework. The second flared portion may extend from the second end toward the first end. In at least some embodiments, the second flared portion may be longitudinally and/or axially spaced apart from the first flared portion by a body portion. In some embodiments, the first flared portion and/or the second flared portion may be configured to exert a radially outward force upon the wall of the first body lumen 10 to prevent migration of the second endoprosthesis 200 within the first body lumen 10.

In some embodiments, the delivery sheath 210 may be an elongate catheter or other tubular shaft suitable for and/or known in the art for delivering endoprostheses. The second endoprosthesis 200 may be disposed within a lumen of the delivery sheath 210 in the radially constrained or collapsed configuration. In the radially constrained or collapsed configuration, the expandable framework may be substantially straight and/or fully elongated. The second endoprosthesis 200 may be deployed from the delivery sheath 210 using one or more known techniques, such as proximally withdrawing the delivery sheath 210 from the second endoprosthesis 200 to expel the second endoprosthesis 200 from the delivery sheath 210. Other techniques may be used to deploy the second endoprosthesis 200 from the delivery sheath 210, which are generally known, but not described in the interest of brevity.

The method may include shifting the second endoprosthesis 200 to the radially expanded configuration within the plurality of loops 130 and/or the passage 150, as seen in FIG. 4. In some embodiments, shifting the second endoprosthesis 200 to the radially expanded configuration may include withdrawing and/or retracting the delivery sheath 210 relative to the second endoprosthesis 200 to expose the second endoprosthesis 200 within the first body lumen 10 and/or within the plurality of loops 130 and/or the passage 150, thereby allowing the second endoprosthesis 200 to radially expand.

In at least some embodiments, the second endoprosthesis 200 and/or the expandable framework may be deployed within a body lumen extending through a stricture to maintain and/or re-establish patency of the body lumen. In some embodiments, the second endoprosthesis 200 and/or the expandable framework may be configured to dilate at least a portion of the body lumen in the radially expanded configuration. For example, second endoprosthesis 200 and/or the expandable framework may be configured to exert a radially outward force upon a wall of the body lumen and/or against a stricture that has formed therein.

In some embodiments, at least a portion of the second endoprosthesis 200 may be disposed within the plurality of loops 130 and/or the passage 150 in the radially expanded configuration. In some embodiments, at least a portion of the second endoprosthesis 200 may extend away from the plurality of loops 130 and/or the passage 150 when the second endoprosthesis 200 is disposed within the plurality of loops 130 and/or the passage 150 in the radially expanded configuration.

In some embodiments, the second endoprosthesis 200 and/or the expandable framework may be configured to engage the plurality of loops 130 and/or the passage 150 in the radially expanded configuration. In the radially expanded configuration, the second endoprosthesis 200 and/or the expandable framework may be configured to exert a radially outward force upon the first endoprosthesis 100 and/or the plurality of loops 130 in the helical configuration and thereby engage the first endoprosthesis 100 and/or the plurality of loops 130 with and/or against a wall of the first body lumen 10. In some instances, portions of the second endoprosthesis 200 extending between adjacent loops 130 may extend radially outward and into contact with the wall of the first body lumen 10.

In some embodiments, the second endoprosthesis 200 may be configured to dilate at least a portion of the first body lumen 10 in the radially expanded configuration. For example, the second endoprosthesis 200 may be configured to exert a radially outward force upon a wall of the first body lumen 10 and/or upon the stricture 14 in the radially expanded configuration. In some embodiments, the second endoprosthesis 200 and/or the expandable framework may be configured to extend across an opening to an adjoining body lumen (e.g., the second body lumen 20). In other words, the second endoprosthesis 200 may be configured to extend across the bifurcation 12 such that a first end region of the second endoprosthesis 200 is placed in the first body lumen 10 upstream of the bifurcation 12 (and across the stricture 14, for example) and a second end region of the second endoprosthesis 200 is placed in the first body lumen 10 downstream of the bifurcation 12.

In some embodiments, the first end portion 110 of the first endoprosthesis 100 may extend away from the second endoprosthesis 200 transversely relative to a central longitudinal axis of the second endoprosthesis 200 when the second endoprosthesis 200 is disposed within the plurality of loops 130 and/or the passage 150 in the radially expanded configuration. In some embodiments, the first end portion 110 of the first endoprosthesis 100 may extend away from the second endoprosthesis 200 into the second body lumen 20 when the second endoprosthesis 200 is disposed within the plurality of loops 130 and/or the passage 150 (which may be positioned in the first body lumen 20 downstream of the bifurcation 12) in the radially expanded configuration.

In some embodiments, the second end portion 112 of the first endoprosthesis 100 may extend away from the second endoprosthesis 200 generally parallel to the central longitudinal axis of the second endoprosthesis 200 when the second endoprosthesis 200 is disposed within the plurality of loops 130 and/or the passage 150 (which may be positioned in the first body lumen 20 downstream of the bifurcation 12) in the radially expanded configuration. In some embodiments, the second end portion 112 of the first endoprosthesis 100 may extend away from the second endoprosthesis 200 within the first body lumen 10 when the second endoprosthesis 200 is disposed within the plurality of loops 130 and/or the passage 150 in the radially expanded configuration.

In some embodiments, the second endoprosthesis 200 may have an outer diameter and/or an outer extent in the radially expanded configuration. In some embodiments, the outer diameter and/or the outer extent of the second endoprosthesis 200 may be within about 20% of the inner diameter 132 of the passage 150. In some embodiments, the outer diameter and/or the outer extent of the second endoprosthesis 200 may be within about 15% of the inner diameter 132 of the passage 150. In some embodiments, the outer diameter and/or the outer extent of the second endoprosthesis 200 may be within about 10% of the inner diameter 132 of the passage 150. In some embodiments, the outer diameter and/or the outer extent of the second endoprosthesis 200 may be within about 5% of the inner diameter 132 of the passage 150. In some embodiments, the outer diameter and/or the outer extent of the second endoprosthesis 200 may be substantially equal to the inner diameter 132 of the passage 150.

In some embodiments, portions of the second endoprosthesis 200 (when radially expanded within the plurality of loops 130 of the first endoprosthesis 100) extending between adjacent loops of the plurality of loops 130 may have a second outer diameter and/or a second outer extent that is greater than the outer diameter and/or the outer extent of the second endoprosthesis 200 disposed within the passage 150 and/or the plurality of loops 130 such that portions of the second endoprosthesis 200 extend radially outward between adjacent loops 130.

In some embodiments, the second endoprosthesis 200 and/or the expandable framework may include a polymeric cover 220 disposed on, disposed over, and/or extending along at least a portion of its length. In some embodiments, the polymeric cover 220 may be disposed on and/or along the first flared portion, the second flared portion, and/or the body portion extending therebetween. In some embodiments, the polymeric cover 220 may be disposed on and/or along an outer surface of the expandable framework. In some embodiments, at least a portion of the expandable framework may be embedded in the polymeric cover 220. In some embodiments, the polymeric cover 220 may be fixedly or releasably secured to, bonded to, or otherwise attached to the expandable framework. In some embodiments, the polymeric cover 220 may be impermeable to fluids, debris, medical instruments, etc. Some suitable but non-limiting materials for the polymeric cover 220 are described below.

In some embodiments, the polymeric cover 220 may extend along an entire length and/or circumference of the second endoprosthesis 200 and/or the expandable framework. In some embodiments, the polymeric cover 220 may extend along a portion of the length of the second endoprosthesis 200 and/or the expandable framework. In some embodiments, the polymeric cover 220 may be discontinuous. In some embodiments, the polymeric cover 220 may extend discontinuously between the first end (e.g., the proximal end) of the second endoprosthesis 200 and/or the expandable framework and the second end (e.g., the distal end) of the second endoprosthesis 200 and/or the expandable framework in the radially expanded configuration. In some embodiments, the polymeric cover 220 may extend continuously from the first end (e.g., the proximal end) of the second endoprosthesis 200 and/or the expandable framework to the second end (e.g., the distal end) of the second endoprosthesis 200 and/or the expandable framework in the radially expanded configuration. Other configurations are also contemplated.

After deployment of the second endoprosthesis 200 within the plurality of loops 130 and/or the passage 150, the second endoprosthesis 200 and the polymeric cover 220, where present, may cooperate with the first endoprosthesis 100 to define a helical fluid path around (e.g., on an exterior of) the second endoprosthesis 200 from the second body lumen 20 into a lower portion of the first body lumen 10. In at least some embodiments, the first endoprosthesis 100 may create gaps 30 between an exterior (e.g., an outer surface) of the second endoprosthesis 200 and the wall of the first body lumen 10, wherein the gaps 30 may define the helical fluid path around the exterior (e.g., outer surface) of the second endoprosthesis 200.

In some embodiments, the first endoprosthesis 100 may be configured to provide drainage from the second body lumen 20 into the first body lumen 10 internally and/or through the lumen 102 of the first endoprosthesis 100. In some embodiments, the first endoprosthesis 100 may cooperate with the second endoprosthesis 200 and the polymeric cover 220, where present, to provide drainage from the second body lumen 20 into the first body lumen 10 externally along and/or using the helical fluid path around the exterior of the second endoprosthesis 200. In some embodiments, the first endoprosthesis 100 may be configured to provide drainage from the second body lumen 20 into the first body lumen 10 both internally (e.g., through the lumen 102 of the first endoprosthesis 100) and externally (e.g., along the exterior of the first endoprosthesis 100 forming the gaps 30 along the exterior of the second endoprosthesis 200).

Figure 6:
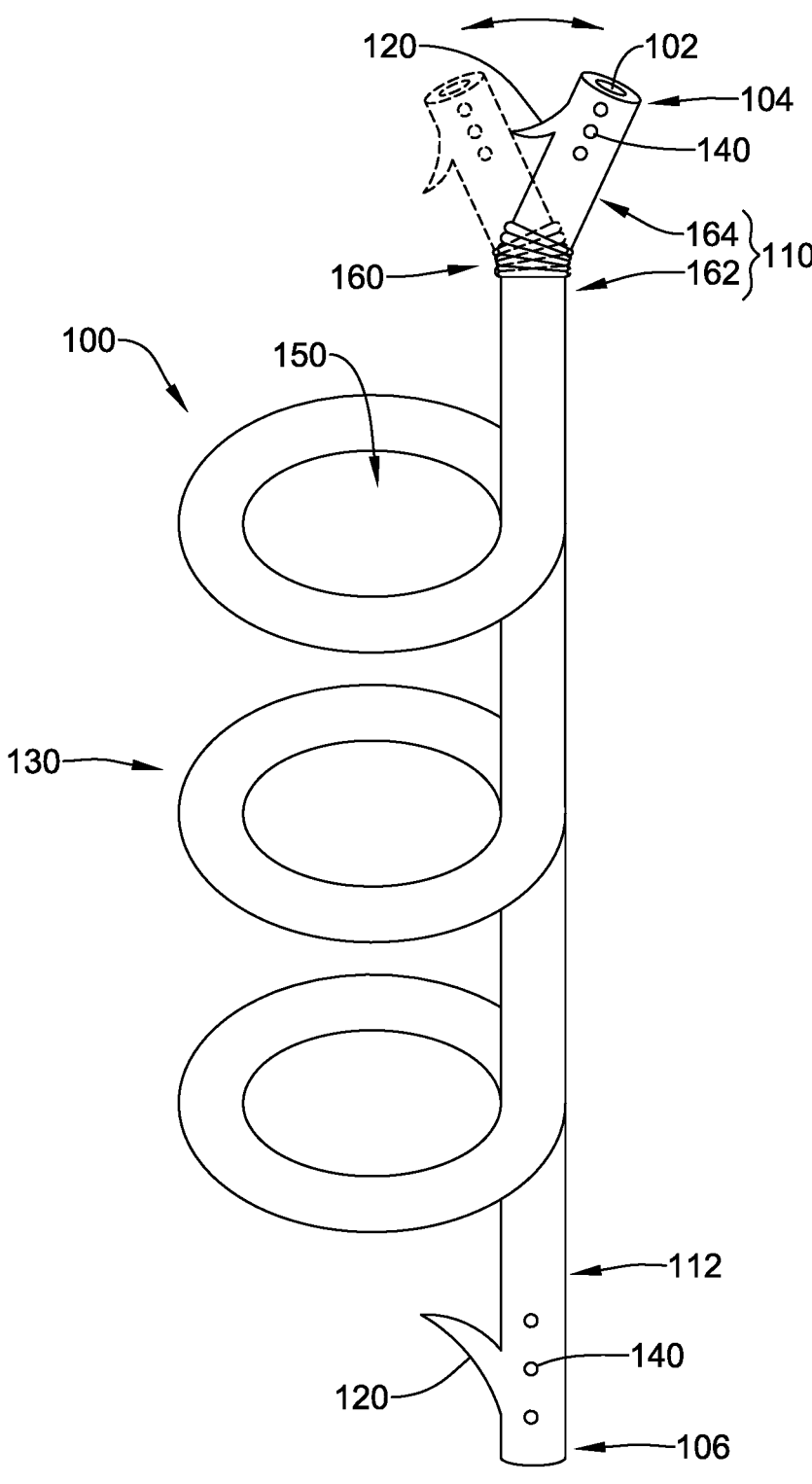
FIG. 6 illustrates selected aspects of an alternative configuration of the stent of FIG. 5.

FIG. 6 illustrates selected aspects of an alternative configuration of the first endoprosthesis 100. In some embodiments, the first endoprosthesis 100 may include a flexible region, such as a corrugated section 160 disposed between the first end 104 and the plurality of loops 130. The flexible region (e.g., the corrugated section 160) may be more flexible that the remainder of the length of the first endoprosthesis 100, including a portion of the tubular member of the first endoprosthesis 100 on both sides of the flexible region. In some embodiments, the first end portion 110 may include the corrugated section 160. In some embodiments, the corrugated section 160 may separate the first end portion 110 into a first section 162 and a second section 164, with the flexible region (e.g., the corrugated section 160) therebetween. In some embodiments, the first section 162 may be disposed proximal of the flexible or corrugated section 160 and/or between the flexible or corrugated section 160 and the plurality of loops 130, and the second section 164 may be disposed distal of the flexible or corrugated section 160 and/or between the flexible or corrugated section 160 and the first end 104.

In some embodiments, the corrugated section 160 may resemble an accordion and/or a bellows. The corrugated section 160 may add an additional aspect of flexibility and/or bendability to the first end portion 110 of the first endoprosthesis 100. In some embodiments, the first endoprosthesis 100 having the corrugated section 160 may be configured to adapt to the irregular nature of tortuous anatomy more readily. In some embodiments, the corrugated section 160 may be configured to bend and/or deflect the second section 164 relative to the first section 162. In other words, the central longitudinal axis of the second section 164 may extend at a non-parallel angle (e.g., an acute, perpendicular or obtuse angle) to the central longitudinal axis of the first section 162. In some embodiments, the second section 164 may bend and/or deflect in a coplanar manner with the first section 162. In some embodiments, the second section 164 may bend and/or deflect askew and/or in a non-coplanar manner to the first section 162. Other configurations are also contemplated.

In some embodiments, the corrugated section 160 may be manipulated by the guidewire 90 during delivery of the first endoprosthesis 100. In some embodiments, the corrugated section 160 may be steerable using a mechanism or mechanisms built into the first endoprosthesis 100. For example, one or more steering wires may be disposed within and/or may extend along the wall of the first endoprosthesis 100. Other configurations are also contemplated.

Figure 7:
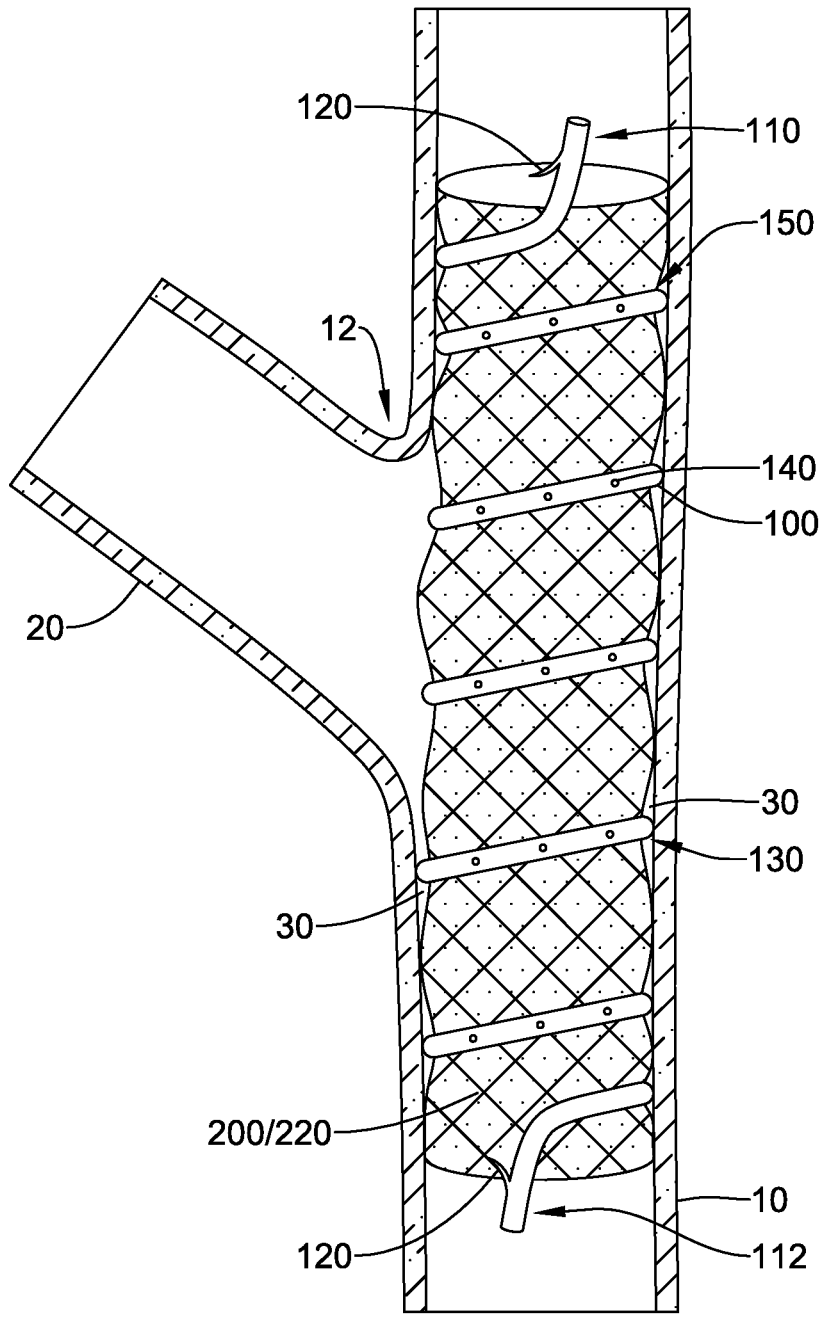
FIG. 7 illustrates selected aspects of a stent system for maintaining patency of a body lumen.

FIG. 7 illustrates selected aspects of an alternative use and/or configuration of the system and/or method for maintaining patency of a body lumen disclosed herein. In some embodiments, the method may include advancing a guidewire into the first body lumen 10 such that the guidewire extends upstream of the bifurcation 12. The method may include advancing the first endoprosthesis 100 into the first body lumen 10 in a straightened configuration over the guidewire to a position in which the first endoprosthesis 100 spans the bifurcation 12 with a distal end region of the first endoprosthesis 100 located in the first body lumen 10 upstream of the bifurcation 12 and a proximal end region of the first endoprosthesis 100 located in the first body lumen 10 downstream of the bifurcation 12. In some embodiments, the first endoprosthesis 100 may be constrained in the straightened configuration by the guidewire when advancing the first endoprosthesis 100 through the first body lumen 10 across the bifurcation 12. In some alternative embodiments, the first endoprosthesis 100 may be constrained in the straightened configuration by a delivery sheath surrounding the first endoprosthesis 100 when advancing the first endoprosthesis 100 through the first body lumen 10 and across the bifurcation 12. Other configurations, including combinations thereof, are also contemplated. In some embodiments, advancing the first endoprosthesis 100 into the first body lumen 10 in the straightened configuration may include positioning the first end portion 110 of the first endoprosthesis 100 in the first body lumen 10 upstream of the bifurcation 12 and the second end portion 112 of the first endoprosthesis 100 in the first body lumen 10 downstream of the bifurcation 12 such that a medial region of the first endoprosthesis 100 spans the bifurcation 12.

The method may include deploying the first endoprosthesis 100 within the first body lumen 10 in a helical configuration defining a plurality of loops 130, as seen in FIG. 7, with the first end portion 110 of the first endoprosthesis 100 in the first body lumen 10 on a first side of the bifurcation 12, such as upstream of the bifurcation 12, and the second end portion 112 of the first endoprosthesis 100 in the first body lumen 10 on a second side of the bifurcation 12, such as downstream of the bifurcation 12. Accordingly, a medial portion of the first endoprosthesis 100 may be located at the bifurcation 12 when deployed into the helical configuration. When deployed into the helical configuration, the medial portion of the first endoprosthesis 100 may define the plurality of helical loops 130. The first endoprosthesis 100 may be configured to automatically shift from the straightened configuration (in which the helical loops 130 are straightened or elongated) when constrained by the guidewire 90 (or an outer sheath, if present) to the helical configuration when unconstrained. In at least some embodiments, the first endoprosthesis 100 may be self-biased toward the helical configuration when unconstrained.

In some embodiments, at least a portion of the first endoprosthesis 100 may extend away from the plurality of loops 130 in the helical configuration. In some embodiments, the first end portion 110 may extend away from the plurality of loops 130 in the helical configuration. In some embodiments, the first end portion 110 may extend from the plurality of loops 130 to the first end 104 of the first endoprosthesis 100. In some embodiments, a second end portion 112 may extend away from the plurality of loops 130 in the helical configuration. In some embodiments, the second end portion 112 may extend from the plurality of loops 130 to the second end 106 of the first endoprosthesis 100.

Once the first endoprosthesis 100 has been delivered and expanded into the helical configuration across the bifurcation 12, the method may then include advancing a second guidewire into the first body lumen 10. The method may further include advancing the second guidewire into and/or through the plurality of helical loops 130 and/or through the passage 150 of the first endoprosthesis 100 subsequent to deploying the first endoprosthesis into the helical configuration. The method may further include advancing a second endoprosthesis 200 into the first body lumen 10 over the second guidewire in a radially collapsed configuration. Thus, the second endoprosthesis 200 may be placed within the helical loops 130 in a radially constrained or collapsed configuration such that the helical loops 130 surround the radially constrained or collapsed second endoprosthesis 200 with the second endoprosthesis 200 extending from a portion of the first body lumen 10 proximal (e.g., downstream) of the bifurcation 12 to a portion of the first body lumen 10 distal (e.g., upstream) of the bifurcation 12. The second endoprosthesis 200 may be positioned such that a distal end region of the second endoprosthesis 200 may extend distal of the bifurcation 12 in the radially constrained or collapsed configuration while a proximal end region of the second endoprosthesis 200 may extend proximal of the bifurcation 12 in the radially constrained or collapsed configuration.

The second endoprosthesis 200 may be configured to shift from the radially collapsed configuration toward a radially expanded configuration. In at least some embodiments, the second endoprosthesis 200 may be self-biased toward the radially expanded configuration. In some embodiments, the second endoprosthesis 200 may be formed from a super-elastic and/or shape memory material, such as nitinol. In some embodiments, the second endoprosthesis 200 may be constrained in the radially collapsed configuration by the properties of the shape memory material when advancing the second endoprosthesis 200 into the first body lumen 10. In some embodiments, the second endoprosthesis 200 may be constrained in the radially collapsed configuration by a delivery sheath surrounding the second endoprosthesis 200 when advancing the second endoprosthesis 200 into the first body lumen 10. Other configurations, including combinations thereof, are also contemplated.

In some embodiments, the delivery sheath may be an elongate catheter or other tubular member suitable for and/or known in the art for delivering endoprostheses. The second endoprosthesis 200 may be disposed within a lumen of the delivery sheath in the radially constrained or collapsed configuration. In the radially collapsed configuration, the expandable framework may be substantially straight and/or fully elongated. The second endoprosthesis 200 may be deployed from the delivery sheath using one or more known techniques, such as proximally withdrawing the delivery sheath from the second endoprosthesis 200 to expel the second endoprosthesis 200 from the delivery sheath. Other techniques may be used to deploy the second endoprosthesis 200 from the delivery sheath, which are generally known, but not described in the interest of brevity.

The method may include shifting the second endoprosthesis 200 to the radially expanded configuration within the plurality of loops 130 and/or the passage 150, as seen in FIG. 7. In some embodiments, shifting the second endoprosthesis 200 to the radially expanded configuration may include withdrawing and/or retracting the delivery sheath relative to the second endoprosthesis 200 to expose the second endoprosthesis 200 within the first body lumen 10 and/or within the plurality of loops 130 and/or the passage 150, thereby allowing the second endoprosthesis 200 to radially expand.

In at least some embodiments, the second endoprosthesis 200 and/or the expandable framework may be deployed within the first body lumen 10 extending through a stricture to maintain and/or re-establish patency of the body lumen 10. In some embodiments, the second endoprosthesis 200 and/or the expandable framework may be configured to dilate at least a portion of the first body lumen 10 in the radially expanded configuration. For example, second endoprosthesis 200 and/or the expandable framework may be configured to exert a radially outward force upon a wall of the first body lumen 10 and/or against a stricture that has formed therein.

In some embodiments, at least a portion of the second endoprosthesis 200 may be disposed within the plurality of loops 130 and/or the passage 150 in the radially expanded configuration. In some embodiments, at least a portion of the second endoprosthesis 200 may extend away from the plurality of loops 130 and/or the passage 150 when the second endoprosthesis 200 is disposed within the plurality of loops 130 and/or the passage 150 in the radially expanded configuration.

In some embodiments, the second endoprosthesis 200 may be configured to engage the plurality of loops 130 and/or the passage 150 in the radially expanded configuration. In the radially expanded configuration, the second endoprosthesis 200 may be configured to exert a radially outward force upon the first endoprosthesis 100 and/or the plurality of loops 130 in the helical configuration and thereby engage the first endoprosthesis 100 and/or the plurality of loops 130 with and/or against a wall of the first body lumen 10. In some instances, portions of the second endoprosthesis 200 extending between adjacent loops 130 may extend radially outward and into contact with the wall of the first body lumen 10.

In some embodiments, the second endoprosthesis 200 may be configured to dilate at least a portion of the first body lumen 10 in the radially expanded configuration. For example, the second endoprosthesis 200 may be configured to exert a radially outward force upon a wall of the first body lumen 10 in the radially expanded configuration. In some embodiments, the first endoprosthesis 100 and the second endoprosthesis 200 may be configured to extend across an opening to an adjoining body lumen (e.g., the second body lumen 20), as shown in FIG. 7. In other words, the second endoprosthesis 200 may be configured to extend across the bifurcation 12 such that a first end region of the second endoprosthesis 200 is placed in the first body lumen 10 upstream of the bifurcation 12 and a second end region of the second endoprosthesis 200 is placed in the first body lumen 10 downstream of the bifurcation 12.

In some embodiments, the first end portion 110 of the first endoprosthesis 100 may extend away from the second endoprosthesis 200 generally parallel to a central longitudinal axis of the second endoprosthesis 200 when the second endoprosthesis 200 is disposed within the plurality of loops 130 and/or the passage 150 in the radially expanded configuration. In some embodiments, the first end portion 110 of the first endoprosthesis 100 may extend away from the second endoprosthesis 200 within the first body lumen 10 when the second endoprosthesis 200 is disposed within the plurality of loops 130 and/or the passage 150 in the radially expanded configuration.

In some embodiments, the second end portion 112 of the first endoprosthesis 100 may extend away from the second endoprosthesis 200 generally parallel to the central longitudinal axis of the second endoprosthesis 200 when the second endoprosthesis 200 is disposed within the plurality of loops 130 and/or the passage 150 in the radially expanded configuration. In some embodiments, the second end portion 112 of the first endoprosthesis 100 may extend away from the second endoprosthesis 200 within the first body lumen 10 when the second endoprosthesis 200 is disposed within the plurality of loops 130 and/or the passage 150 in the radially expanded configuration.

In one example, the first end portion 110 of the first endoprosthesis 100 may extend within the first body lumen 10 upstream from the second endoprosthesis 200 when the second endoprosthesis 200 is disposed within the plurality of loops 130 and/or the passage 150 in the radially expanded configuration, and the second end portion 112 of the first endoprosthesis 100 may extend within the first body lumen 10 downstream from the second endoprosthesis 200 when the second endoprosthesis 200 is disposed within the plurality of loops 130 and/or the passage 150 in the radially expanded configuration. In another example, the first end portion 110 of the first endoprosthesis 100 may extend within the first body lumen 10 downstream from the second endoprosthesis 200 when the second endoprosthesis 200 is disposed within the plurality of loops 130 and/or the passage 150 in the radially expanded configuration, and the second end portion 112 of the first endoprosthesis 100 may extend within the first body lumen 10 upstream from the second endoprosthesis 200 when the second endoprosthesis 200 is disposed within the plurality of loops 130 and/or the passage 150 in the radially expanded configuration.

After deployment of the second endoprosthesis 200 within the plurality of loops 130 and/or the passage 150, the second endoprosthesis 200 and the polymeric cover 220, where present, may cooperate with the first endoprosthesis 100 to define a helical fluid path around (e.g., on an exterior of) the second endoprosthesis 200 from an upper portion (e.g., an upstream portion) of the first body lumen 10 into a lower portion (e.g., a downstream portion) of the first body lumen 10 and from the second body lumen 20 into the lower portion (e.g., a downstream portion) of the first body lumen 10. In at least some embodiments, the first endoprosthesis 100 may create gaps 30 between an exterior (e.g., an outer surface) of the second endoprosthesis 200 and the wall of the first body lumen 10, wherein the gaps 30 may define the helical fluid path around the exterior (e.g., outer surface) of the second endoprosthesis 200. The gaps 30 may be fluidly accessible from the second body lumen 20, thereby maintaining flow of fluid from the second body lumen 20 into the first body lumen 10 along the helical gaps 30 when the first body lumen 10 is treated with the system.

In some embodiments, the first endoprosthesis 100 may cooperate with the second endoprosthesis 200 and the polymeric cover 220, where present, to provide drainage from the second body lumen 20 into the first body lumen 10 externally along and/or using the helical fluid path around the exterior of the second endoprosthesis 200. In some embodiments, the first endoprosthesis 100 may include a plurality of drainage ports 140 formed along a medial portion of the first endoprosthesis 100. The plurality of drainage ports 140 may be in fluid communication with the lumen 102 of the first endoprosthesis 100. The medial portion of the first endoprosthesis 100, including the drainage ports 140, may be positioned across the opening to the second body lumen 20. The plurality of drainage ports 140 may permit fluid from the second body lumen 20 to access and/or flow into the lumen 102 of the first endoprosthesis 100. Accordingly, in some embodiments, the first endoprosthesis 100 may be configured to provide drainage from the second body lumen 20 into the first body lumen 10 internally and/or through the lumen 102 of the first endoprosthesis 100. In some embodiments, the first endoprosthesis 100 may be configured to provide drainage from the second body lumen 20 into the first body lumen 10 both internally (e.g., through the lumen 102 of the first endoprosthesis 100) and externally (e.g., along the exterior of the first endoprosthesis 100 forming the gaps 30 along the exterior of the second endoprosthesis 200).

The materials that can be used for the various components of the system and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the first endoprosthesis, the second endoprosthesis, the expandable framework, the polymeric cover, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane, polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like.

In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system and/or components thereof may also be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothil ones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for maintaining patency of a body lumen, comprising:
   a first endoprosthesis having a lumen extending from a first end to a second end, wherein the first endoprosthesis is configured to shift from a straightened configuration to a helical configuration defining a plurality of loops; and
   a second endoprosthesis configured to shift from a radially collapsed configuration toward a radially expanded configuration;
   wherein the plurality of loops defines a passage having an inner diameter;
   wherein at least a portion of the second endoprosthesis is disposed within the passage in the radially expanded configuration.

2. The system of claim 1, wherein at least a portion of the second endoprosthesis extends away from the passage when the second endoprosthesis is disposed within the passage in the radially expanded configuration.

3. The system of claim 1, wherein at least a portion of the first endoprosthesis extends away from the plurality of loops.

4. The system of claim 3, wherein a first end portion of the first endoprosthesis extends away from the second endoprosthesis transversely relative to a central longitudinal axis of the second endoprosthesis when the second endoprosthesis is disposed within the passage in the radially expanded configuration.

5. The system of claim 3, wherein a second end portion of the first endoprosthesis extends away from the second endoprosthesis generally parallel to a central longitudinal axis of the second endoprosthesis when the second endoprosthesis is disposed within the passage in the radially expanded configuration.

6. The system of claim 1, wherein the first endoprosthesis is formed from a polymeric material.

7. A system for maintaining patency of a body lumen, comprising:
   a first endoprosthesis having a lumen extending from a first end to a second end, wherein the first endoprosthesis is configured to shift from a straightened configuration to a helical configuration defining a plurality of loops; and
   a second endoprosthesis configured to shift from a radially collapsed configuration toward a radially expanded configuration;
   wherein the plurality of loops defines a passage having an inner diameter;
   wherein the second endoprosthesis is configured to be disposed within the passage;
   wherein the second endoprosthesis has an outer diameter in the radially expanded configuration;
   wherein the outer diameter of the second endoprosthesis is within 20% of the inner diameter of the passage.

8. The system of claim 7, wherein the plurality of loops defines an outer diameter between about 6 French and about 12 French.

9. The system of claim 7, wherein the first endoprosthesis is self-biased toward the helical configuration.

10. The system of claim 7, wherein the second endoprosthesis is self-biased toward the radially expanded configuration.

11. The system of claim 7, wherein the second endoprosthesis includes a polymeric covering extending along at least a portion of its length.

12. The system of claim 7, wherein the first endoprosthesis includes a corrugated section disposed between the first end and the plurality of loops.

13. The system of claim 7, wherein the first endoprosthesis includes one or more drainage holes extending through a side wall of the first endoprosthesis.

14. The system of claim 7, wherein the first endoprosthesis includes one or more anti-migration elements extending radially outward therefrom.

15. A method of maintaining patency of a body lumen, comprising:

advancing a first endoprosthesis into a first body lumen in a straightened configuration;

deploying the first endoprosthesis within the first body lumen in a helical configuration defining a plurality of loops;

advancing a second endoprosthesis into the first body lumen in a radially collapsed configuration; and shifting the second endoprosthesis to a radially expanded configuration within the plurality of loops.

16. The method of claim 15, wherein advancing the first endoprosthesis into the first body lumen in the straightened configuration includes positioning a first end portion of the first endoprosthesis in a second body lumen adjacent the first body lumen.

17. The method of claim 16, wherein the first end portion of the first endoprosthesis extends away from the second endoprosthesis transversely relative to a central longitudinal axis of the second endoprosthesis when the second endoprosthesis is disposed within the plurality of loops in the radially expanded configuration.

18. The method of claim 16, wherein the first endoprosthesis is self-biased toward the helical configuration when unconstrained.

19. The method of claim 18, wherein the first endoprosthesis is constrained in the straightened configuration by a guidewire when advancing the first endoprosthesis into the first body lumen.

20. The method of claim 18, wherein the first endoprosthesis is constrained in the straightened configuration by a delivery sheath when advancing the first endoprosthesis into the first body lumen.

\* \* \* \* \*